United States Patent [19]

Bringhurst et al.

[11] Patent Number: Plant 6,558

[45] Date of Patent: Jan. 24, 1989

[54] STRAWBERRY PLANT CALLED 'MUIR'

[75] Inventors: Royce S. Bringhurst, Davis; Victor Voth, Santa Ana, both of Calif.

[73] Assignee: Regents of the University of California, Berkeley, Calif.

[21] Appl. No.: 44,937

[22] Filed: Apr. 30, 1987

[51] Int. Cl.[4] ..... A01H 5/03

[52] U.S. Cl. ..... Plt./49

[58] Field of Search ..... Plt./49

*Primary Examiner*—Robert E. Bagwill

*Attorney, Agent, or Firm*—Townsend and Townsend

[57] ABSTRACT

A new and distinct variety of day-neutral strawberry plant characterized by its capability of high yield of very large firm fruit somewhat similar to 'Selva', but which is less susceptible to two-spotted mite. The variety is adapted to growing in all California fruiting areas where 'Selva' is grown.

2 Drawing Sheets

DESCRIPTION

This invention relates to a new and distinctive day-neutral type strawberry cultivar designated 'Muir' which is the result of a cross between Cal 70.3117 (not patented) and Cal 71.98-605 (not patented) made in 1975. 'Muir' is a sister to 'Selva' (U.S. Plant Pat. No. 5,266). The pedigree is as follows:

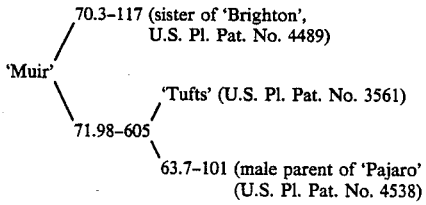

'Muir' first fruited at the University of California Wolfskill Experimental Orchards near Davis in 1977 where it was selected and designated originally as Cal 75.71-105. It was tested later as as advanced selection CN 17.

'Muir' has been propagated asexually by runners and has been tested at various University of California field stations and research facilities and to a limited extent in a few growers fields under Test Agreement.

In the photographs:

Figure 1:
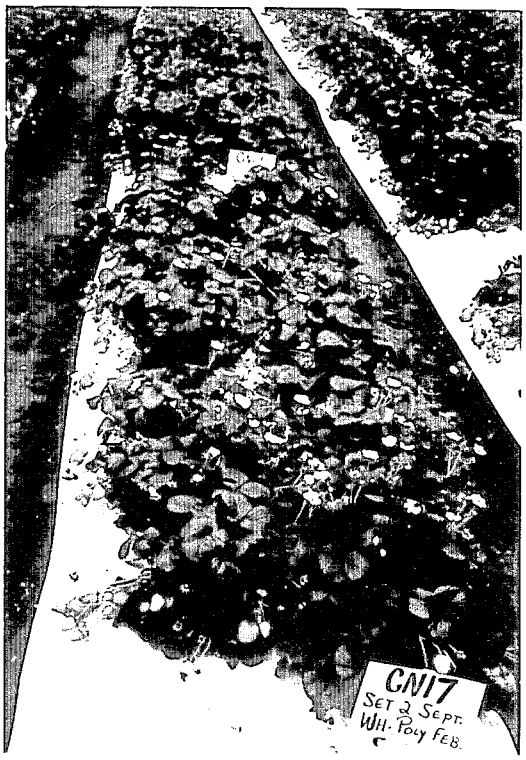
FIG. 1 shows typical growth, flowering and fruiting characteristics of the plant.
Figure 2:
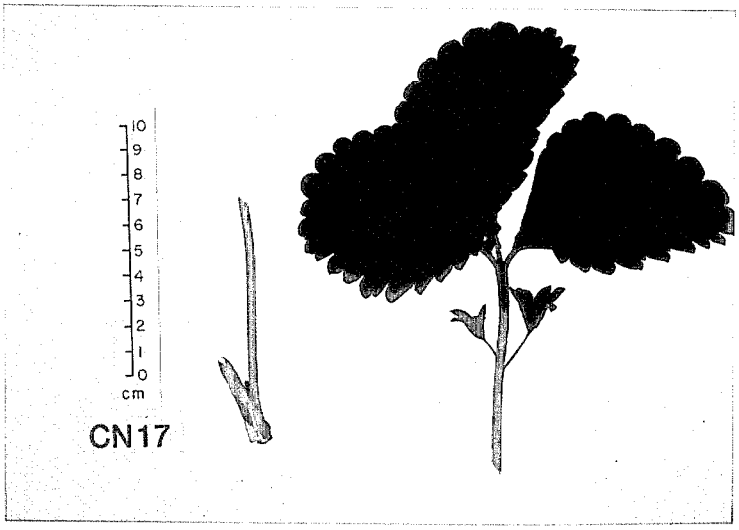
FIG. 2 shows a typical midfall mature leaf from a nursery plant.
Figure 3:
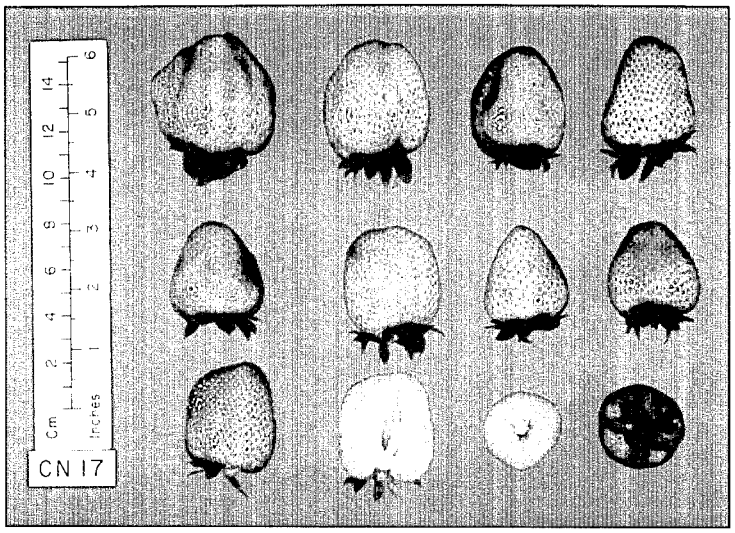
FIG. 3 shows individual representative mid-season fruit with longitudinal and cross-sectional views.

'Muir' commences fruiting about three months after planting, whether fresh dug or cold storage plants are used, regardless of planting time provided that satisfactory growing conditions prevail. 'Muir' is not as strongly day-neutral as 1 Brighton' (U.S. Plant Pat. No. 4,489), 1 Hecker' (U.S. Plant Pat. No. 4,507) or 'Fern' (U.S. Pla nt Pat. No. 3,267) but it is a somewhat stronger day-neutral than 'Selva'. The differences are most evident in the nursery where only the mother and first daughter plants of 'Muir' and 'Selva' tend to flower and fruit strongly, whereas most of the daughter plants of 'Brighton', 'Hecker' and 'Fern' do so. 'Muir' is of interest for winter and summer plantings particularly in all situations where 'Selva' is used successfully.

Plants and foliage: 'Muir' plants are more erect in growth habits than those of 'Selva'. Leaf color and characteristics from late summer nursery plants of 'Muir' are compared with those of 'Selva', 'Fern' and 'Hecker' in Table 1:

TABLE 1

| | MUIR | SELVA | FERN | HECKER |
|---|---|---|---|---|
| Color | 2.5GY4/3 | 7.5GY4/4 | 7.5GY4/4 | 2.5GY4/3 |
| Shape (length/width) | 1.11 | 1.20 | 1.10 | 1.13 |
| Base angle of terminal leaflet | 56° | 51° | 58° | 56° |
| Size of terminal leaflets | 77 | 86 | 70 | 76 |
| Serrations of terminal leaflet | 9.8 | 9.8 | 9.3 | 8.0 |
| Petiolule length (MM) | 7.4 | 11.4 | 7.7 | 9.3 |
| Petiolule length (MM) | 167 | 161 | 155 | 137 |
| Bract leaflet position | 71 | 68 | 61 | 64 |

As shown above 'Muir' leaves are darker and less yellow than those of 'Selva' and 'Fern' and about the same color as those of 'Hecker' (Munsell Color System —Nickerson Color Fan). Terminal leaflets are somewhat similar in shape to those of 'Fern' and 'Hecker' and more round than those of 'Selva' as shown by the length/width measurement and half-blade terminal leaflet basal angle. 'Muir' terminal leaflets are about the same size as those of 'Hecker', larger than those of 'Fern' and smaller than those of 'Selva' as determined by extracting the square root of the length x width measurements. Terminal leaflet serration numbers are greater on 'Muir' than 'Fern' and 'Hecker' but abut the same for 'Muir' and 'Selva' but distinctively more indented on 'Muir' than 'Selva'. Petiolules (terminal leaflet stems) of 'Muir' are considerably shorter than those of 'Selva' and 'Hecker' about equal to those of 'Fern'. 'Muir' plants are slightly larger than those of 'Selva' and considerably larger than those of 'Fern' 'Hecker' as indicated by petiole length. Bract leaflets occur on may of the petioles of 'Muir' and 'Selva' in about the same position 71% and 68% respectively, up the length of the petiole; higher up than on 'Fern' (61%) or 'Hecker'

(64%) both of which have a lower frequency of the bract leaflets. Runner production in nursery plants of 'Muir' is very good, about equal to that of 'Selva', somewhat better than 'Fern' or 'Hecker'.

Isozymes in leaf extracts: 'Muir' has been classified for three enzyme systems by starch gel electrophoresis: A. Phosphoglucoisomerase (PGI): B. Leucine amino peptidase (LAP) and C. Phosphoglucomutase (PGM): they compare with the other day-neutral California cultivars as follows:

TABLE 2

| | MUIR | SELVA | FERN | HECKER | APTOS & BRIGHTON |
|---|---|---|---|---|---|
| PGI | A2 | A2 | A4 | A1 | A4 |
| LAP | B1 | B3 | B3 | B1 | B3 |
| PGM | C2 | C2 | C2 | C4 | C4 |

'Muir' and 'Selva' differ for PGI in the intensity of the slowest band; in 'Selva' the band (A2) is intense and does not segregate while in 'Muir' the slowest band (A2) is faint and segregates 1:1 in a backcross. (For the procedure see: J. Amer Soc. HortSci. 106:684–687, 1981). 'Muir' can thus be distinguished unambiguously from any of the other California bay-neutral cultivars by using the three enzyme systems.

Disease and pest reaction: 'Muir' is highly resistant to (tolerant of) the virus diseases common in California including "Mild Yellow Edge" and complexes containing it, quite susceptible to Verticillum wilt, moderately susceptible to common leaf spot (Ramularia) and appears to be considerably less susceptible to two-spotted mite than 'Selva'.

Flowering, fruiting, fruit and production characteristics: 'Muir' is similar to California day-neutral cultivar 'Selva' in that with a minimum of conditioning, it will flower and fruit anytime, effectively independent of day length. Flowers are borne on long, relatively thick peduncles, more erect than those of 'Selva' and they tend to remain so until the weight of the fruit brings them down. The flowers have large attractive petals (5 to 7), are self-fertile with ample pollen throughout the season and pollination is generally good with relatively few malformed fruit.

The fruit shape is medium to long conic, slightly bulbous and sometimes flat or wedgy; centers may be hollow. 'Muir' yield and midseason fruit and quality characteristics are compared with those of 'Selva', 'Fern' and 'Hecker' as grown under optimum conditions under the "hill" system in winter plantings at the University of California Strawberry Research Facility, Watsonville in Table 3 as follows:

TABLE 3

| | MUIR | SELVA | FERN | HECKER |
|---|---|---|---|---|
| Yield (GR/Plant) | 1528 | 1557 | 1502 | 1556 |
| Size (GR/Fruit) | 24.8 | 25.9 | 22.4 | 16.2 |
| Firmness | 6.4 | 6.8 | 5.4 | 5.3 |
| Color | 7R4.5/13 | 7R4/11 | 5R3.5/12 | 7.5R4.5/13 |
| Ascorbic acid | 27.2 | 24.1 | 27.8 | 46.7 |
| Soluble solids | 7.8 | 8.1 | 7.9 | 7.6 |

'Muir' is capable of yielding about as much as other high-yielding day-neutral cultivars. Fruit size averages nearly as large as that of 'Selva', larger than 'Fern' and much larger than 'Hecker'. Size varies considerably, depending upon the season and the environmental conditions. 'Muir' fruit is somewhat less firm than that of 'Selva' but considerably firmer than 'Fern' or 'Hecker' as measured by a pentetrometer equipped with a "Hunter Force Gage" and it handles about as well as 'Selva'. The fruit skin color is similar to that of 'Selva' but slightly less intense and less red than that of 'Fern' (ibid.). The finish is particularly bright and attractive. The flesh is about the same as the skin but less intense with a slightly lighter ring around the core. The achenes are bright yellow to slightly reddish, positioned about flush with the skin surface. The calyx is medium to large sized, positioned from even with the base of the fruit to being borne on a short rather thick neck, somewhat reflexed. 'Muir' fruit averages at least as high an ascorbic acid content as 'Selva' or 'Fern' but considerably less than 'Hecker' as measured by the Loeffler and Ponting method (1942, J. Indust. and Engin. Chem. 14:846). Soluble solids measurements were not significantly different from those of the comparison cultivars. The flavor of 'Muir' fruit is as good or better than that of 'Selva' and is slightly more juicy. The fruit is recommended for fresh market and proceeding, for commercial planting and home gardening, particularly where "off season" fruiting is desired. The only cultivar that it resembles closely in performance is 'Selva' and consequently it is of interest whenever 'Selva' is currently used.

We claim:

1. The new distinct variety of strawberry plant herein described and illustrated and identified by the characteristics enumerated above together with the parts thereof.

* * * * *